United States Patent [19]
Tanaka et al.

[11] Patent Number: 5,286,638
[45] Date of Patent: Feb. 15, 1994

[54] PEROXIDASE GENE OF MICROBIAL ORIGIN

[75] Inventors: Yoshikazu Tanaka; Toshihiko Ashikari, both of Osaka; Haruyo Hatanaka, Kyoto; Yuji Shibano, Osaka; Teruo Amachi, Hyogo; Toru Nakayama; Motoo Sumida, both of Osaka, all of Japan

[73] Assignee: Suntory Limited of 1-40, Dojimahama, Osaka, Japan

[21] Appl. No.: 792,259

[22] Filed: Nov. 15, 1991

[30] Foreign Application Priority Data

Nov. 16, 1990 [JP] Japan ................... 2-310415
Apr. 26, 1991 [JP] Japan ................... 3-097615

[51] Int. Cl.$^5$ .............. C12N 15/53; C12N 9/08; C12N 15/81; C12N 15/70
[52] U.S. Cl. ..................... 435/192; 435/69.1; 435/69.8; 435/71.1; 435/71.2; 435/172.3; 435/252.3; 435/252.33; 435/320.1; 435/254.2; 536/23.74; 935/14; 935/28; 935/29; 935/56; 935/69; 935/73
[58] Field of Search ............ 536/27, 23.74; 435/69.1, 69.8, 71.1, 71.2, 172.3, 192, 252.3, 252.33, 255, 320.1; 935/14, 28, 29, 56, 69, 73

[56] References Cited

U.S. PATENT DOCUMENTS 5,137,822  8/1992  Yabusaki et al. .............. 435/193

FOREIGN PATENT DOCUMENTS 0171074  2/1986  European Pat. Off. .
WO-A-9216634  10/1992  PCT Int'l Appl. .

OTHER PUBLICATIONS

Ortlepp, S. A. et al. "Expression and Characterization of a ... " J. Biotechnol. 11:353–364 (1989).
Belyavsky, A. et al. "PCR-based cDNA library construction ... " Nuc. Acids Res. 17(8) 2919–2932 (Apr. 1989).
Berger, S. L. et al. "Guide to Molecular Cloning Techniques" (1987) Meth. in Enzynol. 152:393–399, 415–423, 432–447, 661–704.
Deutscher, M. P. "Guide to Protein Purification" Meth. in Enzynol. 182:602–613, 738–751 (1990).
Saloheimo, Markku et al. "A Lingin Peroxidase-Encoding cDNA from the White-Rot Fungus Phlebia Radiata; Charaterization and Expression in Trichoderma Reesei", Gene 85 (1989) pp. 343–351.
Fishel, Laurence A., et al., "Yeast Cytochrome c Peroxidase; Mutagenesis and Expression in Escherichia Coli Show Tryptophan-51 is Not the Radical Site in Compound I", Biochemestry, vol. 26, (1987) pp. 351–360.
Saloheimo, Markku et al., "Heterologous Production of a Ligninolytic Enzyme; Expression of the Phlebia Radiata Laccase Gene in Trichoderma Reesei", Biotechnology, vol. 9, (1991) pp. 987–990.

*Primary Examiner*—Robert A. Wax
*Assistant Examiner*—Rebecca Prouty
*Attorney, Agent, or Firm*—Cushman, Darby & Cushman

[57] ABSTRACT

A peroxidase gene derived from *Arthromyse ramosus* and its cloning and expression in *E. coli* and yeast is disclosed. The peroxidase encoded by this gene is not-specific and does not contain isozymes and hence is suitable as a diagnostic reagent or as a marker enzyme in enzyme innunoassays.

2 Claims, 7 Drawing Sheets

CODE
E:EcoRI, H:HindIII, S:SalI,
Ap:AMPICILLIN RESISTANCE GENE,
pGAP: GLYCERALDEHYDE-3-PHOSPHATE DEHYDROGENASE GENE PROMOTER,
TRP1: YEAST TRP1 GENE,
IR: INVERTED REPEAT SEQUENCE,
POD: cDNA OF A.ramosus PEROXIDASE

Fig. 1

CODE

E: EcoRI, H: HindII, B: BamHI, G: BglII, S: SalI,

Ap: AMPICILLIN RESISTANCE GENE,

Tc: TETRACYCLINE RESISTANCE GENE,

TRP1: YEAST TRP1 GENE,

ARS: YEAST AUTONOMOUSLY REPLICATING SEQUENCE

IR: INVERTED REPEAT SEQUENCE

Fig. 2

CODE

E: EcoRI, H: HindIII, S: SalI,

Ap: AMPICILLIN RESISTANCE GENE,

GAPDH: GLYCERALDEHYDE-3-PHOSPHATE
DEHYDROGENASE GENE, pGAP: GLYCERALDEHYDE-3-PHOSPHATE
DEHYDROGENASE GENE PROMOTER,

TRP1: YEAST TRP1 GENE,

IR: INVERTED REPEAT SEQUENCE

Fig. 3

CODE

E: EcoRI, H: HindIII, S: SalI,

Ap: AMPICILLIN RESISTANCE GENE, pGAP: GLYCERALDEHYDE-3-PHOSPHATE DEHYDROGENASE GENE PROMOTER,

TRP1: YEAST TRP1 GENE,

IR: INVERTED REPEAT SEQUENCE,

POD: cDNA OF A. ramosus PEROXIDASE

```
AAACCCACCT GTTCTACTAC TAGTCCTCTT CCATTTTGTA TTTGAACGCT GTTTCCGACG     60

TCAAGAACGA CAACT ATG AAG CTC TCG CTT TTC TCC ACC TTC GCT GCT GTC    111
              Met Lys Leu Ser Leu Phe Ser Thr Phe Ala Ala Val
                1           5                  10
ATC ATC GGT GCT CTC GCT CTC CCC CAG GGT CCT GGA GGA GGC GGG         159
Ile Ile Gly Ala Leu Ala Leu Pro Gln Gly Pro Gly Gly Gly Gly
        15              20                  25
TCA GTC ACT TGC CCG GGT GGA CAG TCC ACT TCG AAC AGC CAG TGC TGC     207
Ser Val Thr Cys Pro Gly Gly Gln Ser Thr Ser Asn Ser Gln Cys Cys
        30              35                  40
GTC TGG TTC GAC GTT CTA GAC GAT CTT CAG ACC AAC TTC TAC CAA GGG     255
Val Trp Phe Asp Val Leu Asp Asp Leu Gln Thr Asn Phe Tyr Gln Gly
 45              50                  55                  60
TCC AAG TGT GAG AGC CCT GTT CGC AAG ATT CTT AGA ATT GTT TTC CAT     303
Ser Lys Cys Glu Ser Pro Val Arg Lys Ile Leu Arg Ile Val Phe His
                65                  70                  75
GAC GCG ATC GGA TTT TCG CCG GCG TTG ACT GCT GCT GGT CAA TTC GGT     351
Asp Ala Ile Gly Phe Ser Pro Ala Leu Thr Ala Ala Gly Gln Phe Gly
        80                  85                  90
GGT GGA GGA GCT GAT GGC TCC ATC ATT GCG CAT TCG AAC ATC GAA TTG     399
Gly Gly Gly Ala Asp Gly Ser Ile Ile Ala His Ser Asn Ile Glu Leu
        95                  100                 105
GCC TTC CCG GCT AAT GGC GGC CTC ACC GAC ACC ATC GAA GCC CTC CGC     447
Ala Phe Pro Ala Asn Gly Gly Leu Thr Asp Thr Ile Glu Ala Leu Arg
    110                 115                 120
GCG GTC GGT ATC AAC CAC GGC GTC TCT TTC GGC GAT CTC ATC CAA TTC     495
Ala Val Gly Ile Asn His Gly Val Ser Phe Gly Asp Leu Ile Gln Phe
125                 130                 135                 140
GCC ACT GCC GTC GGC ATG TCC AAC TGC CCT GGC TCT CCT CGA CTT GAG     543
Ala Thr Ala Val Gly Met Ser Asn Cys Pro Gly Ser Pro Arg Leu Glu
                145                 150                 155
```

Fig. 5(b)

```
TTC TTG ACG GGA AGA AGC AAC AGT TCC CAG CCC TCC CCT CCT TCG CTG         591
Phe Leu Thr Gly Arg Ser Asn Ser Ser Gln Pro Ser Pro Pro Ser Leu
            160                 165                 170
ATC CCG GGT CCT GGA AAC ACT GTC ACT GCT ATC TTG GAT CGT ATG GGC         639
Ile Pro Gly Pro Gly Asn Thr Val Thr Ala Ile Leu Asp Arg Met Gly
            175                 180                 185
GAT GCA GGC TTC AGC CCT GAT GAA GTC GTT GAC TTG CTT GCT GCG CAT         687
Asp Ala Gly Phe Ser Pro Asp Glu Val Val Asp Leu Leu Ala Ala His
            190                 195                 200
AGT TTG GCT TCT CAG GAA GGT TTG AAC TCG GCT ATT TTC AGG TCG CCT         735
Ser Leu Ala Ser Gln Glu Gly Leu Asn Ser Ala Ile Phe Arg Ser Pro
205                 210                 215                 220
TTG GAC TCG ACC CCT CAA GTT TTC GAT ACC CAG TTC TAT ATC GAG ACC         783
Leu Asp Ser Thr Pro Gln Val Phe Asp Thr Gln Phe Tyr Ile Glu Thr
            225                 230                 235
TTG CTC AAG GGA ACC ACT CAG CCC GGA CCC TCT CTC GGC TTT GCA GAG         831
Leu Leu Lys Gly Thr Thr Gln Pro Gly Pro Ser Leu Gly Phe Ala Glu
            240                 245                 250
GAG CTC TCC CCC TTC CCT GGT GAA TTC CGC ATG AGG TCC GAC GCT CTC         879
Glu Leu Ser Pro Phe Pro Gly Glu Phe Arg Met Arg Ser Asp Ala Leu
            255                 260                 265
TTG GCT CGC GAC TCC CGA ACC GCC TGC CGA TGG CAA TCC ATG ACC AGC         927
Leu Ala Arg Asp Ser Arg Thr Ala Cys Arg Trp Gln Ser Met Thr Ser
            270                 275                 280
AGC AAT GAA GTT ATG GGC CAG CGA TAC CGC GCC GCC ATG GCC AAG ATG         975
Ser Asn Glu Val Met Gly Gln Arg Tyr Arg Ala Ala Met Ala Lys Met
285                 290                 295                 300
TCT GTT CTC GGC TTC GAC AGG AAC GCC CTC ACC GAT TGC TCT GAC GTT        1023
Ser Val Leu Gly Phe Asp Arg Asn Ala Leu Thr Asp Cys Ser Asp Val
            305                 310                 315
ATT CCT TCT GCT GTG TCC AAC AAC GCT GCT CCT GTT ATC CCT GGT GGC        1071
Ile Pro Ser Ala Val Ser Asn Asn Ala Ala Pro Val Ile Pro Gly Gly
            320                 325                 330
```

Fig. 5(c)

```
CTT ACT GTC GAT GAT ATT GAG GTT TCG TGC CCG AGC GAG CCT TTC CCT      1119
Leu Thr Val Asp Asp Ile Glu Val Ser Cys Pro Ser Glu Pro Phe Pro
        335                 340                 345
GAA ATT GCT ACC GCC TCA GGC CCT CTC CCC TCC CTC GCT CCT GCT CCT      1167
Glu Ile Ala Thr Ala Ser Gly Pro Leu Pro Ser Leu Ala Pro Ala Pro
        350                 355                 360
TGATCTGGTG AAGATGGTAC ATCCTGCTCT CTCACGATCC CTCTTAGCTA TTTATCCAAT    1227

CTATCTACCT ATCTATGCAG TTTCTGTCCA CCCTCAGTTA TGAATATGAC TTGGTTATCT    1287

GTGTATCCGA CTCGGTGCTT GGCAGCACGT GTATGATATT ATATAATCAA TCATGAACGC    1347

ATTCCTCCGT GTGGGAGTGT GCGTCTTTCT CTCGGAG                             1384
```

5,286,638

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO:1:

```
Gln Gly Pro Gly Gly Gly Gly Gly Ser Val Thr Cys Pro Gly Gly Gln
  1               5                  10                  15
        Ser Thr Ser Asn
                 20
```

( 2 ) INFORMATION FOR SEQ ID NO:2:

( i ) SEQUENCE CHARACTERISTICS:
        ( A ) LENGTH: 30 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:2:

Ala Val Gly Ile Asn His Gly Val Ser Phe Gly Asp Leu Ile Gln Phe
1               5                   10                  15

Ala Thr Ala Val Gly Met Ser Asn Cys Pro Gly Ser Pro Arg
        20                  25                  30

(2) INFORMATION FOR SEQ ID NO:3:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:3:

Ser Asn Ser Ser Gln Pro Ser Pro Ser Leu Ile Pro Gly Pro Gly
1               5                   10                  15

Asn Thr Val Thr Ala Ile Leu Asp Arg
        20                  25

(2) INFORMATION FOR SEQ ID NO:4:

(i) SEQUENCE CHARACTERISTICS:
    (A) LENGTH: 22 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:4:

Gly Thr Thr Gln Pro Gly Pro Ser Leu Gly Phe Ala Glu Glu Leu Ser
1               5                   10                  15

Pro Phe Pro Gly Glu Phe
        20

(2) INFORMATION FOR SEQ ID NO:5:

(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:5:

Thr Ala Cys Arg Trp Gln Ser Met Thr Ser Ser Asn Glu Val
1               5                   10

(2) INFORMATION FOR SEQ ID NO:6:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:6:

Met Ser Val Leu Gly Phe Asp Arg
1               5

( 2 ) INFORMATION FOR SEQ ID NO:7:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Ala Ala Pro Val Ile Pro Gly Gly Leu Thr Val Asp
1               5                   10

( 2 ) INFORMATION FOR SEQ ID NO:8:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

CCCTGCAGGA TCCATGTGGC AAGTCGATCA TGAC        34

( 2 ) INFORMATION FOR SEQ ID NO:9:

( i ) SEQUENCE CHARACTERISTICS:
    ( A ) LENGTH: 5 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:9:

Trp Gln Ser Met Thr
1               5

( 2 ) INFORMATION FOR SEQ ID NO:10:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:10:

GCGAGCTCGG TACCCGGGTT TTTTTTTTT TTTTT        35

( 2 ) INFORMATION FOR SEQ ID NO:11:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

TAAATAGAAT TCATGGTTA        19

( 2 ) INFORMATION FOR SEQ ID NO:12:

( i ) SEQUENCE CHARACTERISTICS:

(A) LENGTH: 345 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:12:

```
Xaa Gln Gly Pro Gly Gly Gly Gly Ser Val Thr Cys Pro Gly Gly
 1               5                  10                  15

Gln Ser Thr Ser Asn Ser Gln Cys Cys Val Trp Phe Asp Val Leu Asp
                20                  25                  30

Asp Leu Gln Thr Asn Phe Tyr Gln Gly Ser Lys Cys Glu Ser Pro Val
            35                  40                  45

Arg Lys Ile Leu Arg Ile Val Phe His Asp Ala Ile Gly Phe Ser Pro
        50                  55                  60

Ala Leu Thr Ala Ala Gly Gln Phe Gly Gly Gly Gly Ala Asp Gly Ser
65                  70                  75                  80

Ile Ile Ala His Ser Asn Ile Glu Leu Ala Phe Pro Ala Asn Gly Gly
                85                  90                  95

Leu Thr Asp Thr Ile Glu Ala Leu Arg Ala Val Gly Ile Asn His Gly
            100                 105                 110

Val Ser Phe Gly Asp Leu Ile Gln Phe Ala Thr Ala Val Gly Met Ser
        115                 120                 125

Asn Cys Pro Gly Ser Pro Arg Leu Glu Phe Leu Thr Gly Arg Ser Asn
130                 135                 140

Ser Ser Gln Pro Ser Pro Pro Ser Leu Ile Pro Gly Pro Gly Asn Thr
145                 150                 155                 160

Val Thr Ala Ile Leu Asp Arg Met Gly Asp Ala Gly Phe Ser Pro Asp
                165                 170                 175

Glu Val Val Asp Leu Leu Ala Ala His Ser Leu Ala Ser Gln Glu Gly
            180                 185                 190

Leu Asn Ser Ala Ile Phe Arg Ser Pro Leu Asp Ser Thr Pro Gln Val
        195                 200                 205

Phe Asp Thr Gln Phe Tyr Ile Glu Thr Leu Leu Lys Gly Thr Thr Gln
    210                 215                 220

Pro Gly Pro Ser Leu Gly Phe Ala Glu Glu Leu Ser Pro Phe Pro Gly
225                 230                 235                 240

Glu Phe Arg Met Arg Ser Asp Ala Leu Leu Ala Arg Asp Ser Arg Thr
                245                 250                 255

Ala Cys Arg Trp Gln Ser Met Thr Ser Ser Asn Glu Val Met Gly Gln
            260                 265                 270

Arg Tyr Arg Ala Ala Met Ala Lys Met Ser Val Leu Gly Phe Asp Arg
        275                 280                 285

Asn Ala Leu Thr Asp Cys Ser Asp Val Ile Pro Ser Ala Val Ser Asn
    290                 295                 300

Asn Ala Ala Pro Val Ile Pro Gly Gly Leu Thr Val Asp Asp Ile Glu
305                 310                 315                 320

Val Ser Cys Pro Ser Glu Pro Phe Pro Glu Ile Ala Thr Ala Ser Gly
                325                 330                 335

Pro Leu Pro Ser Leu Ala Pro Ala Pro
            340                 345
```

(2) INFORMATION FOR SEQ ID NO:13:

(i) SEQUENCE CHARACTERISTICS:
(A) LENGTH: 20 amino acids
(B) TYPE: amino acid
(C) STRANDEDNESS: single ( D ) TOPOLOGY: linear ( i i ) MOLECULE TYPE: peptide ( x i ) SEQUENCE DESCRIPTION: SEQ ID NO:13:

```
Met Lys Leu Ser Leu Phe Ser Thr Phe Ala Ala Val Ile Ile Gly Ala
 1               5                  10                  15
Leu Ala Leu Pro
            20
```

( 2 ) INFORMATION FOR SEQ ID NO:14:

( i ) SEQUENCE CHARACTERISTICS:
        ( A ) LENGTH: 1032 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:14:

```
CAGGGTCCTG GAGGAGGAGG CGGGTCAGTC ACTTGCCCGG GTGGACAGTC CACTTCGAAC      60
AGCCAGTGCT GCGTCTGGTT CGACGTTCTA GACGATCTTC AGACCAACTT CTACCAAGGG     120
TCCAAGTGTG AGAGCCCTGT TCGCAAGATT CTTAGAATTG TTTTCCATGA CGCGATCGGA     180
TTTTCGCCGG CGTTGACTGC TGCTGGTCAA TTCGGTGGTG GAGGAGCTGA TGGCTCCATC     240
ATTGCGCATT CGAACATCGA ATTGGCCTTC CCGGCTAATG GCGGCCTCAC CGACACCATC     300
GAAGCCCTCC GCGCGGTCGG TATCAACCAC GGCGTCTCTT CGGCGATCT  CATCCAATTC     360
GCCACTGCCG TCGGCATGTC CAACTGCCCT GGCTCTCCTC GACTTGAGTT CTTGACGGGA     420
AGAAGCAACA GTTCCCAGCC CTCCCCTCCT TCGCTGATCC GGGTCCTGG  AAACACTGTC     480
ACTGCTATCT TGGATCGTAT GGGCGATGCA GGCTTCAGCC CTGATGAAGT CGTTGACTTG     540
CTTGCTGCGC ATAGTTTGGC TTCTCAGGAA GGTTTGAACT CGGCTATTTT CAGGTCGCCT     600
TTGGACTCGA CCCCTCAAGT TTTCGATACC CAGTTCTATA TCGAGACCTT GCTCAAGGGA     660
ACCACTCAGC CCGGACCCTC TCTCGGCTTT GCAGAGGAGC TCTCCCCCTT CCCTGGTGAA     720
TTCCGCATGA GGTCCGACGC TCTCTTGGCT CGCGACTCCC GAACCGCCTG CCGATGGCAA     780
TCCATGACCA GCAGCAATGA AGTTATGGGC CAGCGATACC GCGCCGCCAT GGCCAAGATG     840
TCTGTTCTCG GCTTCGACAG GAACGCCCTC ACCGATTGCT CTGACGTTAT TCCTTCTGCT     900
GTGTCCAACA ACGCTGCTCC TGTTATCCCT GGTGGCCTTA CTGTCGATGA TATTGAGGTT     960
TCGTGCCCGA GCGAGCCTTT CCCTGAAATT GCTACCGCCT CAGGCCCTCT CCCCTCCCTC    1020
GCTCCTGCTC CT                                                        1032
```

( 2 ) INFORMATION FOR SEQ ID NO:15:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear     ( i i ) MOLECULE TYPE: DNA (genomic)

( x i ) SEQUENCE DESCRIPTION: SEQ ID NO:15:

```
ATGAAGCTCT CGCTTTTCTC CACCTTCGCT GCTGTCATCA TCGGTGCTCT CGCTCTCCCC    60
```

( 2 ) INFORMATION FOR SEQ ID NO:16:

( i ) SEQUENCE CHARACTERISTICS:
        ( A ) LENGTH: 1384 base pairs
        ( B ) TYPE: nucleic acid (C) STRANDEDNESS: single
(D) TOPOLOGY: linear (ii) MOLECULE TYPE: DNA (genomic)

(xi) SEQUENCE DESCRIPTION: SEQ ID NO:16:

| | | | | | | |
|---|---|---|---|---|---|---|
| AAACCCACCT | GTTCTACTAC | TAGTCCTCTT | CCATTTTGTA | TTTGAACGCT | GTTTCCGACG | 60 |
| TCAAGAACGA | CAACTATGAA | GCTCTCGCTT | TTCTCCACCT | TCGCTGCTGT | CATCATCGGT | 120 |
| GCTCTCGCTC | TCCCCCAGGG | TCCTGGAGGA | GGAGGCGGGT | CAGTCACTTG | CCCGGGTGGA | 180 |
| CAGTCCACTT | CGAACAGCCA | GTGCTGCGTC | TGGTTCGACG | TTCTAGACGA | TCTTCAGACC | 240 |
| AACTTCTACC | AAGGGTCCAA | GTGTGAGAGC | CCTGTTCGCA | AGATTCTTAG | AATTGTTTTC | 300 |
| CATGACGCGA | TCGGATTTTC | GCCGGCGTTG | ACTGCTGCTG | GTCAATTCGG | TGGTGGAGGA | 360 |
| GCTGATGGCT | CCATCATTGC | GCATTCGAAC | ATCGAATTGG | CCTTCCCGGC | TAATGGCGGC | 420 |
| CTCACCGACA | CCATCGAAGC | CCTCCGCGCG | GTCGGTATCA | ACCACGGCGT | CTCTTTCGGC | 480 |
| GATCTCATCC | AATTCGCCAC | TGCCGTCGGC | ATGTCCAACT | GCCCTGGCTC | TCCTCGACTT | 540 |
| GAGTTCTTGA | CGGGAAGAAG | CAACAGTTCC | CAGCCCTCCC | CTCCTTCGCT | GATCCCGGGT | 600 |
| CCTGGAAACA | CTGTCACTGC | TATCTTGGAT | CGTATGGGCG | ATGCAGGCTT | CAGCCCTGAT | 660 |
| GAAGTCGTTG | ACTTGCTTGC | TGCGCATAGT | TTGGCTTCTC | AGGAAGGTTT | GAACTCGGCT | 720 |
| ATTTTCAGGT | CGCCTTTGGA | CTCGACCCCT | CAAGTTTTCG | ATACCCAGTT | CTATATCGAG | 780 |
| ACCTTGCTCA | AGGGAACCAC | TCAGCCCGGA | CCCTCTCTCG | GCTTTGCAGA | GGAGCTCTCC | 840 |
| CCCTTCCCTG | GTGAATTCCG | CATGAGGTCC | GACGCTCTCT | TGGCTCGCGA | CTCCCGAACC | 900 |
| GCCTGCCGAT | GGCAATCCAT | GACCAGCAGC | AATGAAGTTA | TGGGCCAGCG | ATACCGCGCC | 960 |
| GCCATGGCCA | AGATGTCTGT | TCTCGGCTTC | GACAGGAACG | CCCTCACCGA | TTGCTCTGAC | 1020 |
| GTTATTCCTT | CTGCTGTGTC | CAACAACGCT | GCTCCTGTTA | TCCCTGGTGG | CCTTACTGTC | 1080 |
| GATGATATTG | AGGTTTCGTG | CCCGAGCGAG | CCTTTCCCTG | AAATTGCTAC | CGCCTCAGGC | 1140 |
| CCTCTCCCCT | CCCTCGCTCC | TGCTCCTTGA | TCTGGTGAAG | ATGGTACATC | CTGCTCTCTC | 1200 |
| ACGATCCCTC | TTAGCTATTT | ATCCAATCTA | TCTACCTATC | TATGCAGTTT | CTGTCCACCC | 1260 |
| TCAGTTATGA | ATATGACTTG | GTTATCTGTG | TATCCGACTC | GGTGCTTGGC | AGCACGTGTA | 1320 |
| TGATATTATA | TAATCAATCA | TGAACGCATT | CCTCCGTGTG | GGAGTGTGCG | TCTTTCTCTC | 1380 |
| GGAG | | | | | | 1384 |

(2) INFORMATION FOR SEQ ID NO:17:

(i) SEQUENCE CHARACTERISTICS:
(A) LENGTH: 364 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

```
Met Lys Leu Ser Leu Phe Ser Thr Phe Ala Ala Val Ile Ile Gly Ala
 1               5                  10                  15

Leu Ala Leu Pro Gln Gly Pro Gly Gly Gly Gly Ser Val Thr Cys
                20              25                  30

Pro Gly Gly Gln Ser Thr Ser Asn Ser Gln Cys Cys Val Trp Phe Asp
            35                  40                  45

Val Leu Asp Asp Leu Gln Thr Asn Phe Tyr Gln Gly Ser Lys Cys Glu
        50                  55                  60

Ser Pro Val Arg Lys Ile Leu Arg Ile Val Phe His Asp Ala Ile Gly
65                  70                  75                  80
```

```
Phe Ser Pro Ala Leu Thr Ala Ala Gly Gln Phe Gly Gly Gly Ala
                85                  90                  95
Asp Gly Ser Ile Ile Ala His Ser Asn Ile Glu Leu Ala Phe Pro Ala
               100                 105                110
Asn Gly Gly Leu Thr Asp Thr Ile Glu Ala Leu Arg Ala Val Gly Ile
           115                 120             125
Asn His Gly Val Ser Phe Gly Asp Leu Ile Gln Phe Ala Thr Ala Val
    130             135                 140
Gly Met Ser Asn Cys Pro Gly Ser Pro Arg Leu Glu Phe Leu Thr Gly
145             150                 155                 160
Arg Ser Asn Ser Ser Gln Pro Ser Pro Pro Ser Leu Ile Pro Gly Pro
                165                 170                 175
Gly Asn Thr Val Thr Ala Ile Leu Asp Arg Met Gly Asp Ala Gly Phe
            180                 185                 190
Ser Pro Asp Glu Val Val Asp Leu Leu Ala Ala His Ser Leu Ala Ser
        195                 200                 205
Gln Glu Gly Leu Asn Ser Ala Ile Phe Arg Ser Pro Leu Asp Ser Thr
    210                 215                 220
Pro Gln Val Phe Asp Thr Gln Phe Tyr Ile Glu Thr Leu Leu Lys Gly
225                 230                 235                 240
Thr Thr Gln Pro Gly Pro Ser Leu Gly Phe Ala Glu Glu Leu Ser Pro
            245                 250                 255
Phe Pro Gly Glu Phe Arg Met Arg Ser Asp Ala Leu Leu Ala Arg Asp
        260                 265                 270
Ser Arg Thr Ala Cys Arg Trp Gln Ser Met Thr Ser Ser Asn Glu Val
    275                 280                 285
Met Gly Gln Arg Tyr Arg Ala Ala Met Ala Lys Met Ser Val Leu Gly
290                 295                 300
Phe Asp Arg Asn Ala Leu Thr Asp Cys Ser Asp Val Ile Pro Ser Ala
305                 310                 315                 320
Val Ser Asn Asn Ala Ala Pro Val Ile Pro Gly Gly Leu Thr Val Asp
                325                 330                 335
Asp Ile Glu Val Ser Cys Pro Ser Glu Pro Phe Pro Glu Ile Ala Thr
            340                 345                 350
Ala Ser Gly Pro Leu Pro Ser Leu Ala Pro Ala Pro
            355                 360
```

PEROXIDASE GENE OF MICROBIAL ORIGIN

BACKGROUND OF THE INVENTION

1. Field of the Invention

This invention relates to a cDNA encoding a peroxidase originating from a microorganism (*Arthromyces ramosus*) and a process for producing the peroxidase by use of host cells containing said gene.

2. Prior Art

In recent years, peroxidases, which are enzymes capable of oxidizing various compounds in the presence of hydrogen peroxide, have been used in the same way as various other oxidases as a clinical diagnostic reagent in assays of glucose, cholesterol, phospholipids, urea and so forth. These enzymes have also been used as a labelled enzyme in enzyme linked immunoassays. They have mainly been produced from plants such as horseradish and Japanese radish. However peroxidases originating from these plants contain isozymes having slightly differing properties from each other, and which therefore require considerable labour costs in order to purify them to such a degree that they are usable as a diagnostic reagent.

On the other hand, some peroxidases of microbial origin have been known. However cytochrome c peroxidases and NADH peroxidases produced by bacteria or fungi are unsuitable as a clinical or diagnostic reagent from the viewpoint of the specificity thereof, since they are generally less specific than the common ones originating from horseradish or Japanese radish. Recently, peroxidases capable of acting on o-dianisidine as a hydrogen donor have been produced from *Eschelichia coli* or microorganisms belonging to the genus Myrothecium. However this enzyme is also unsuitable for the aforesaid diagnostic use due to the carcinogenic nature of o-dianisidine.

Under these circumstances, the present inventors conducted research to obtain a naturally occurring peroxidase of microbial origin, which is usable as, for example, a clinical diagnostic reagent or a labelled enzyme in enzyme linked immunoassays similar to conventional ones originating from horseradish or Japanese radish. The inventors have already reported a peroxidase produced by a fungus belonging to the genus Arthromyces, which peroxidase has the desired properties (Japanese Patent Laid-Open No. 43987/1986). They further clarified that the peroxidase of the genus Arthromyces is far superior to conventional peroxidases in terms of chemiluminescence generating activity in the case of determining with chemiluminescent reagent, for example, peroxides, as a clinical diagnostic reagent or a labelled enzyme in an enzyme linked immunoassay (refer to Japanese Patent Laid-Open No. 219398/1988).

SUMMARY OF THE INVENTION

Although the Arthromyces peroxidase is an ideal enzyme to be used as a clinical diagnostic reagent or in an enzyme linked immunoassay as described above, the problem was that this peroxidase cannot be produced at a reasonable cost. This is because a large scale culture of a fungus such as Arthromyces, is very difficult. In addition, it was desired to reveal the amino acid sequence of the enzyme protein in order to understand the action mechanism of the enzyme at a molecular level. The clarification of the amino acid sequence further should make it possible to modify the peroxidase at a molecular level, namely, by using protein engineering techniques.

In order to solve these and other problems, genetic engineering would be the most suitable approach. However the gene encoding the aforesaid peroxidase of Arthromyces origin hitherto has not been obtained. Thus it was impossible to produce said enzyme on a large scale or to modify the same by use of protein engineering techniques.

BRIEF DESCRIPTION OF THE DRAWINGS

FIGS. 5(*a*), (*b*) and (*c*) illustrate the nucleotide sequence of the cDNA of Arthromyces peroxidase including portions of the 3' and 5' non-coding regions (see SEQ ID NO:16). The amino acid sequence encoded by the cDNA is also given.

DETAILED DESCRIPTION OF THE INVENTION

The present inventors have conducted extensive studies in order to solve the above problems. As a result, they have successfully obtained a cDNA of Arthromyces peroxidase and clarified the nucleotide sequence of said gene and the amino acid sequence of said enzyme, thus completing the present invention. Thus it has become possible to produce the Arthromyces peroxidase on a large scale in an appropriate host such as *E. coli* or a yeast which is easy to grow and further to modify said peroxidase by genetic engineering techniques.

Accordingly, the present invention provides a peroxidase gene of Arthromyces origin or a variant or a mutant thereof having a substantially identical biological activity, a recombinant vector containing said gene, host cells transformed with such a plasmid containing said gene and a process for producing the peroxidase by growing said transformants.

The peroxidase gene of the present invention may be obtained from a fungus belonging to the genus Arthromyces. For example, Arthromyces ramosus, which was named SAM 003 and deposited with the Fermentation Research Institute, Agency of Industrial Science and Technology under the accession number of FERM BP-838, is available therefor. In addition, there may be some other microorganisms capable of producing a peroxidase which has a substantially identical biological activity to that of the peroxidase produced by the fungus of the genus Arthromyces. Such microorganisms are also employable as the starting material in the present invention.

The term "substantially identical" used herein is intended to mean that, with regard to the characteristics of the peroxidase encoded by the gene of the present invention, any enzyme which has substantially the same biological activity as the enzyme obtained by the process described in Japanese Patent Laid-Open No. 43987/1986 and has the preferable characteristics described in Japanese Patent Laid-Open No. 219398/1988 is encompassed herein.

Isolation of the mRNA from the aforesaid starting microorganism, preparation of a cDNA library and screening of said library may be performed by a known method, e.g., the one described in Molecular Cloning, second ed., (by Sambrook et al., Cold Spring Harbor, 1988). For example, the gene encoding the peroxidase of the present invention can be obtained in the following manner.

At first, polyA RNAs are extracted from Arthromyces cells. From the polyA RNAs as templates, cDNAs can be prepared to be inserted into a phage cloning vector (for example, λgt10) which is then used to transform a host such as E. coli. Next, the resulting cDNA library is screened by use of a synthetic DNA probe corresponding to the partial amino acid sequence of the peroxidase. Thus positive clones containing a DNA fragment encoding the target peroxidase are selected. The DNA probe to be used in the screening can be synthesized by purifying the peroxidase protein from a culture of Arthromyces by the method as described hereinafter. The amino acid sequences of at least some portions thereof are determined, whereby an appropriate probe can be chosen based on said sequences. Furthermore, a longer probe fragment can be prepared by the polymerase chain reaction (PCR) techniques.

When the full-length cDNA cannot be obtained in the positive clones, a longer cDNA may be prepared by the following procedure. Namely, the phage DNA is prepared from one of the positive clones and an appropriate EcoRI fragment from the phage DNA can be used to screen the same library. Thus several positive clones will be obtained. These positive phage clones are digested with EcoRI and the separated DNA fragments are subcloned into an appropriate vector (for example, M13mp18 or M13mp19). The nucleotide sequences of the thus inserted DNA fragments are determined by, for example, the dideoxy sequencing method.

On the other hand, in order to reveal the full-length cDNA of the peroxidase, the purified peroxidase protein are analyzed to determine the amino acid composition and the amino acid sequences in the amino and carboxyl terminal regions and the results are compared with the amino acid sequence deduced from the nucleotide sequence of the DNA as determined by the aforesaid method.

Examples of the host cells for expressing the cDNA include bacteria such as E. coli and Bacillus subtilis, yeasts and fungi.

The peroxidase of the present invention can be produced by host cells which have been transformed with a plasmid containing the peroxidase gene, preferably in combination with the signal sequence for said gene, together with an appropriate promoter and a terminator. For example, the aforesaid transformant is cultured in a medium containing a suitable carbon source, nitrogen source and trace metal elements in accordance with the method of Shinmen et al. (Agric. Biol. Chem., 50, 247-249, 1986). The target enzyme is purified from the cell extract or, preferably, from the culture supernatant by a combination of known purification procedures such as precipitation, absorption, filtration through a molecular sieve and electrophoresis. For example, the cell extract or the culture supernatant is subjected to ammonium sulfate precipitation (at approximately 75% saturation) followed by a combination of column chromatography steps (e.g., DEAE-cellulose column chromatography and Ultrogel AcA44 column chromatography). Thus the peroxidase of the invention can be obtained. It is expected that the peroxidase thus obtained has excellent characteristics similar to the one described in Japanese Patent Laid-Open No. 43987/1986.

EXAMPLES

To further illustrate the present invention, the following non-limiting Examples will be given, wherein all test procedures were performed in accordance with the method described in Molecular Cloning, Second ed., (by Sambrook et al., Cold Spring Harbor, 1988), unless otherwise stated.

EXAMPLE 1

Analysis of the amino acid composition of the peroxidase protein

The amino acid composition of the peroxidase protein was analyzed by use of a commercial peroxidase of Arthromyces origin (available from Suntory, Ltd.). First, the amino acid composition was analyzed by a conventional method described in detail in Seikagaku Jikken Koza 1, Tanpakushitsu no Kagaku II (by Takahashi, Ikenaka, et al., Tokyo Kagaku Dojin) and Zoku Seikagaku Jikken Koza 2, Tanpakushitsu no Kagaku (Vol. 1) (by Tsunazawa, Sakiyama, et al.). First, 5 nmole of the peroxidase protein was sealed in a glass tube together with 6N hydrochloric acid and hydrolyzed at 110° C. for 24 hours. Then the free PTH-amino acids contained in the reaction mixture were quantitated in an amino acid analyzer (Hitachi Automatic Amino Acid Analyzer 835) to determine the amino acid composition (refer to Table 1).

TABLE 1

| Amino acid | (mole/mol protein) | Amino acid | (mole/mol protein) |
|---|---|---|---|
| Asx* | 34.42 (33)*** | Ile | 15.74 (17) |
| Thr | 19.64 (20) | Leu | 28.89 (28) |
| Ser | 35.48 (38) | Tyr | 3.75 (3) |
| Glx** | 29.26 (28) | Phe | 17.18 (18) |
| Pro | 27.08 (29) | Lys | 4.21 (4) |
| Gly | 36.11 (38) | His | 4.62 (4) |
| Ala | 35.54 (33) | Arg | 15.15 (15) |
| Val | 19.52 (19) | CMC | 8.57 (8) |
| Met | 6.66 (7) | | |

*: Asx represents the total of Asn and Asp.
**: Glx represents the total of Gln and Glu.
***: Each of the figures given in the parenthesis represents the amino acid number calculated on the basis of the nucleotide sequence.

In order to study the amino acid sequence from the amino terminus of the peroxidase protein, the protein was carboxymethylated under reducing conditions, followed by purifying by reverse phase HPLC. Namely, 100 mg (2.5 μmole) of the peroxidase was dissolved in 3.0 ml of a denaturation buffer solution [Tris.HCl (pH 8.5) containing 6M Gdn.HCl, 10 mM EDTA.2 Na) and incubated at 50° C. for 1 hour. Next, 143 μmole (10 μl) of 2-mercaptoethanol was added thereto and the atmosphere of the reaction system was replaced by nitrogen. After an incubation at 37° C. for 1 hour, 150 μl of 1M sodium iodoacetate (dissolved in the denaturation buffer solution, 0.207 g/ml) was added and the mixture was adjusted to pH 8.0 to 8.5 with NaOH. After introducing a nitrogen stream in the reaction system, the mixture was incubated in the dark at 37° C. for 1 hour. During this period, the pH value of the reaction system was maintained at 8.0 to 8.5. After the completion of the reaction, the reaction mixture was thoroughly dialyzed against H$_2$O. The dialyzate was subjected to reverse phase HPLC under the following conditions and the protein fractions were collected, concentrated and lyophilized:

reverse HPLC conditions: column=Zorbax Pro10 PROTEIN PLUS 20 φ;
flow rate=4.0 ml/min.;
mobile phase: A=0.05% TFA in H$_2$O, B=CH$_3$CN, A:B=8:2 (v/v);
detection: A$_{280}$ The yield of the protein was 16%. As a result of SDS-PAGE, only two protein molecular species (molecular weight: approximately 40 K and 30 K) were detected from the protein fraction.

The amino acid sequence of the N-terminal region of of the carboxymethylated peroxidase protein obtained above (5 nmol) was analyzed with a gas phase protein sequencer (Shimadzu Seisakusho, Ltd.). As a result, no free PTH-amino acid was detected, which indicated that the N-terminal amino acid was protected. Thus the N-terminus of the carboxymethylated peroxidase protein was deprotected in the following manner.

An aqueous solution of the carboxymethylated peroxidase (100 nmol/ml) was concentrated to 100 nmol/0.5 ml while blowing a nitrogen stream thereto. Then 30 μl of a reaction buffer solution (0.25M sodium phosphate buffer solution, 0.05M EDTA, 5 mM 2-mercaptoethanol) was added and the resulting mixture was adjusted to pH 7 with NaOH. Pyroglutamyl peptidase was added thereto by 85 units (5 μl of the commercial preparation from *Bacillus Amyloliquefaciens* (Sigma Co.)) and the mixture was reacted at 37° C. for 18 hours. A 60 μl aliquot of the reaction mixture (12 nmol of peroxidase) was applied to the sequencer in two portions to determine the amino acid sequence.

As a result, the protected residue at the N-terminal was revealed to be pyroglutamyl and further the amino acid sequence of the first 20 residues in the N-terminal region was determined as follows. [This corresponds to positions 21 (Gln) to 40 (Asn) in FIG. 5]:

(Gln)-Gly-Pro-Gly-Gly-Gly-Gly-Gly-Ser-Val-Thr-Cys-Pro-Gly-Gly-Gln-Ser-Thr-Ser-Asn;

wherein (Gln) represents a pyroglutamic acid residue (see SEQ ID NO:1)

Next, the partial amino acid sequences of the peroxidase protein were determined by the following method.

The carboxymethylated peroxidase (48 nmol, 1.9 mg) was suspended in 100 μl of 0.1M NH$_4$HCO$_3$ (pH 7.9), to which 2 μl of a 1% solution of TPCK-Trypsin (Worthington) in 0.0024N HCl was added and the mixture was incubated at 35° C. for 6 hours. White clouding in the liquid disappeared immediately after the addition of the enzyme and the solution became clear. After the completion of the reaction, the mixture was lyophilized to stop the reaction. The dry residue was dissolved in 70% formic acid to be provided to the next step of HPLC.

The peptide fragments of the trypsin digest were separated by reverse phase HPLC under the following conditions:

column=Bakerbond Widepore C$_4$ (350 Å), 6 φ×250;
flow rate=1.0 ml/min;
pressure=80 kg/cm$^2$;
temperature=ambient;
mobile phase: A=0.05% TFA in H$_2$O, B=CH$_3$CN, A:B=8:2 (v/v);
detection: A$_{220}$.

Each peak was further purified by reverse HPLC. Then the amino acid sequences of the purified peptides were determined. The sequences of the following 6 peptides were determined as follows by a gas phase protein sequencer (Shimadzu Seisakusho, Ltd.). [These peptides respectively correspond to the regions in FIG. 5 as follows: peptide 1: positions from 125 (Ala) to 154 (Arg); peptide 2: positions from 162 (Ser) to 186 (Arg); peptide 3: positions from 240 (Gly) to 261 (Phe); peptide 4: positions from 275 (Thr) to 288 (Val); peptide 5: positions from 300 (Met) to 307 (Arg); and peptide 6: positions from 325 (Ala) to 336 (Asp).]

Peptide 1:
Ala—Val—Gly—Ile—Asn—His—Gly—Val—Ser—Phe—Gly—Asp—Leu—Ile—Gln—Phe—Ala—Thr—Ala—Val—Gly—Met—Ser—Asn—Cys—Pro—Gly—Ser—Pro—Arg Peptide 2:
Ser—Asn—Ser—Ser—Gln—Pro—Ser—Pro—Pro—Ser—Leu—Ile—Pro—Gly—Pro—Gly—Asn—Thr—Val—Thr—Ala—Ile—Leu—Asp—Arg Peptide 3:
Gly—Thr—Thr—Gln—Pro—Gly—Pro—Ser—Leu—Gly—Phe—Ala—Glu—Glu—Leu—Ser—Pro—Phe—Pro—Gly Glu—Phe Peptide 4:
Thr—Ala—Cys—Arg—Trp—Gln—Ser—Met—Thr—Ser—Ser—Asn—Glu—Val Peptide 5:
Met—Ser—Val—Leu—Gly—Phe—Asp—Arg Peptide 6:
Ala—Ala—Pro—Val—Ile—Pro—Gly—Gly—Leu—Thr—Val—Asp

EXAMPLE 2

Cloning of Arthromyces Peroxidase cDNA (1) Preparation of a cDNA library

Cells of *Arthromyces ramosus* strain were ground in liquid nitrogen in a mortar. From the ground cells, a RNA fraction was prepared by the method using guanidine thiocyanate/caesium chloride. Further, polyA.RNA fraction was separated therefrom by use of oligo(dT)cellulose. The details of the guanidine thiocyanate/caesium chloride method and the purification of polyA.RNA by oligo(dT)cellulose can be found in, for example, R. McGookin, Robert J. Slater et al. (Methods in Molecular Biology, vol. 2, Humana Press Inc., 1984).

To be more specific, to the ground cells obtained above were added, 4 times by volume in total of 5M guanidine thiocyanate, 50 mM Tris-HCl (pH 7.5), 10 mM EDTA and 5% β-mercaptoethanol, and the resulting mixture was further ground. Then N-lauroylsarcosine and caesium chloride were added and dissolved in the ground mixture in such a manner as to respectively give the final concentrations of 4% (w/v) and 0.15 g/ml. Thereafter, the mixture was centrifuged at 10,000 g for 20 minutes to give a supernatant. 5.7M caesium chloride and 0.1M EDTA (pH 7.5) were introduced into a centrifugal tube and the aforesaid supernatant was laminated thereon, followed by centrifuging at 20° C. at 100,000 g for 18 hours with a Hitachi Rotator RPS28-A. After removing the supernatant, the residual precipitate was dissolved in 10 mM Tris-HCl (pH 7.5). Then 6M ammonium acetate and ethanol were added thereto in such a manner as to respectively provide the final concentrations of 4% (v/v) and 70% (v/v). After being allowed to stand at −80° C. overnight, the mixture was centrifuged to recover the precipitate which was then washed with 70% ethanol, dried under a reduced pressure and dissolved in sterilized water. To this solution, 10M lithium chloride was added at the final concentration of 2M. After allowing the mixture to stand in ice-/water for 4 hours, a RNA fraction was yielded.

The RNAs were then fractionated in an oligo(dT)cellulose column. Namely, a column was packed with oligo(dT)cellulose and equilibrated with 1×column binding solution [20 mM Tris-HCl (pH 7.5), 1 mM EDTA, 0.5M NaCl, 0.2% SDS]. Next, the RNA precipitate was dissolved in a column eluting solution [20 mM Tris-HCl (pH 7.5), 1 mM EDTA, 0.2% SDS] and incubated at 65° C. for 5 minutes. An equal volume of 2×column binding solution was added and the solution was passed through the oligo (dT) cellulose column which had been equilibrated. After the column was washed with 1×column binding solution, the column eluting solution was introduced, whereby a RNA fraction was eluted and recovered. To this fraction, 2M sodium acetate was added at the final concentration of 0.15M. After being allowed to stand at −80° C. overnight, the mixture was centrifuged. The precipitate thus formed was washed twice with 70% ethanol, dried under a reduced pressure and dissolved in sterilized water.

The polyA.RNAs thus obtained were used as the templates to prepare cDNAs with a commercial cDNA synthesizing kit "cDNA Synthesis System Plus" (Amersham, Co.) in accordance with the recommendation by the manufacturer. The resulting cDNAs were inserted into the $E.$ $coli$ phage vector λgt10 and the vector was then introduced into an $E.$ $coli$ strain such as C600HF1 (available from Clone Tech, Co.) to thereby give a cDNA library. In the production of the cDNA library, a commercial kit "cDNA cloning system λgt10" (Amersham, Co.) was used in accordance with the recommendations by the manufacturer.

(2) Screening by use of synthetic DNA fragments

The synthetic DNA fragments used in this example had nucleotide sequences presumed based on a partial amino acid sequence of the peroxidase and they were synthesized with a DNA Synthesizer 371A (Applied Bio-System, Co.).

Cloning of a partial cDNA as a screening probe

First, in order to clone a partial fragment of the peroxidase gene a PCR reaction was performed as follows. The complementary chains were synthesized from the polyA.RNAs purified above by a cDNA synthesis kit. The resulting cDNA were amplified by the PCR reaction with a use of a set of synthetic DNA fragments 5'-CCCTGCAGGATCCATGTGGCA(AG)TC-(GATC)ATGAC-3', (see SEQ ID NO:8) comprising a linker region and a nucleotide sequence corresponding to the partial amino acid sequence Trp-Gln-Ser-Met-Thr, and (see SEQ ID NO:9) one other synthetic DNA fragment 5'-GCGAGCTCG-GTACCCGGGTTTTTTTTTTTTTTTTTTT-3', (see SEQ ID NO:10) comprising a linker region and a polyT chain. The reaction mixture was prepared by using GeneAmp TMKit (Takara Shuzo Co., Ltd.) in accordance with the instructions given in the kit. A cycle comprising reaction at 94° C. for 1.5 minutes, at 45° C. for 2.5 minutes and at 72° C. for 3.4 minutes was repeated 25 times. Then the amplified cDNA were cleaved with KpnI and BamHI and cloned into plasmid M13mp18 and M13mp19. The restriction sites were those present in the primers existing at each end. As a result of the sequencing of these clones, a clone containing a nucleotide sequence corresponding to the partial amino acid sequence of the peroxidase in addition to the primer sequences was identified. Thus a partial fragment of the peroxidase gene could be obtained.

Screening

A DNA fragment (approximately 0.4 kb) containing the partial sequence of the peroxidase gene was used as a probe, and a cDNA library of approximately 5,000 clones was screened in the following manner. The λgt10 cDNA library was plated in such a manner as to give approximately 1,000 plaques per plate and the plates were incubated at 37° C. Each plate was covered with a nylon membrane (Amersham, Co.) which was pinholed at several points with an injection needle so as to memorize the relative locations of the membrane and the plate. Next, the membrane was removed and it was layered with the plaques upside on a filter paper which had been impregnated with a denaturation solution (1.5M NaCl, 0.5M NaOH). After being allowed to stand as such for 7 minutes, the membrane was layered on a filter paper impregnated with a neutralization solution (1.5M NaCl, 0.5M Tris-HCl, pH 7.2, 0.001M EDTA) and allowed to stand for 5 minutes. After air-drying, the membrane was placed on an UV trans-illuminator with the plaque side downward and irradiated for 2 to 5 minutes to thereby fix the DNA.

The DNA-DNA hybridization was performed in accordance with the method of Jeffrey and Flavell (Cell 12: 439-439, 1977). Namely, the membrane filter, on which the DNA had been fixed, was immersed in a hybridization solution (6×SSC, 5×Denhard's solution, 0.5% SDS, 10 μg/ml salmon sperm DNA) at 65° C. for 30 minutes. Then the membrane was placed into a thick nylon bag and the probe DNA labeled with $^{32}P$ ($10^6$ to $10^8$ cpm/μg) was added thereto. After a reaction in the hybridization solution at 65° C. for 16 to 20 hours, and the subsequent removal of the hybridization solution, the membrane filter was washed in a washing buffer solution [5×SSC, 0.1% SDS (W/V)] at 65° C. for 15 minutes four times. The membrane filter was then dried and subjected to autoradiography at −80° C. with X-ray film and a sensitized paper sheet.

As a result, 6 positive clones were obtained. Among these clones, C1 and C2 containing longer insertion fragments were cleaved with EcoRI and subcloned into M13mp18. The method for the subcloning will be described hereinafter. When the insertion fragments were analyzed with DNA sequencer Genesis 2000 (du Pont), further nucleotide regions corresponding to the remaining partial amino acid sequences were found. Thus the region of the gene extending between the point approximately 0.5 kb upstream of the cDNA obtained by the PCR reaction and the polyA region, was acquired.

In order to obtain the full-length cDNA, a cDNA library of approximately 50,000 clones was screened with the N-terminal region (about 400 bp) of the C2 clone as a probe by the same method as the one described above. Among 20 positive clones thus obtained, C11 and C13 clones having longer insertion fragments were digested with EcoRI and subcloned into M13mp18. As a result of the sequencing thereof, a nucleotide sequence corresponding to the amino acid sequence at the N-terminal was found.

(3) Subcloning

Phage DNA was prepared from each positive clone obtained above in accordance with the instructions attached to the λgt10 kit. After being digested with EcoRI, the phage DNA was subjected to agarose gel electrophoresis. After the completion of the electrophoresis, the appropriate fragment was excised from the gel and the DNA was collected and purified by using Gene Clean (Bio 101, Co.) in accordance with the instructions given therein. After being extracted with phenol/chloroform and precipitated with ethanol, the DNA was ligated with *E. coli* phage vector M13mp18, which had been digested with EcoRI and dephosphorylated with an alkaline phosphatase, and used to transform *E. coli* strain JM109.

(4) Comparison of nucleotide sequence with amino acid sequence

Figure 5A:
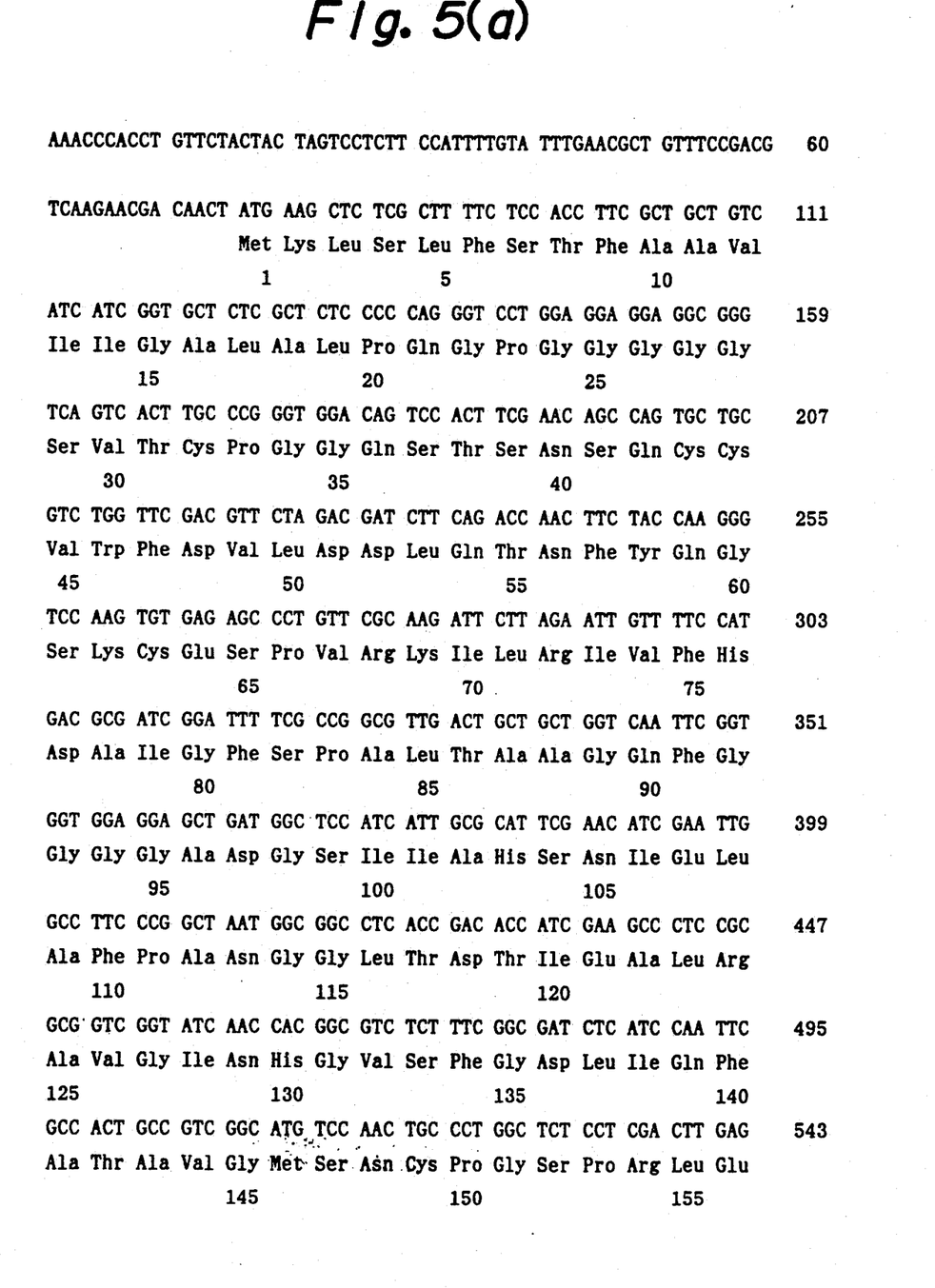
Figure 5C:
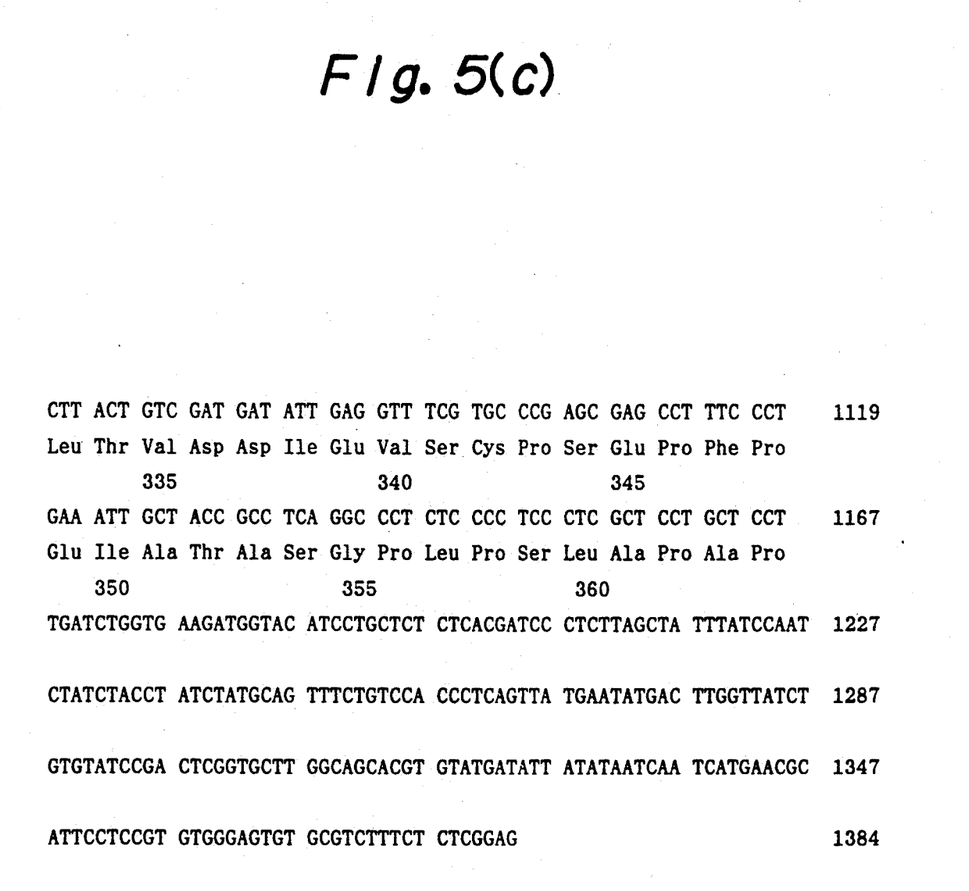

In the peroxidase cDNA, the encoding region corresponded to an amino acid sequence consisting of 364 residues and ranged from the initiator codon ATG to the terminator codon TGA given in FIG. 5. The amino acid sequence in the amino terminal region of the peroxidase as determined in Example 1 initiated with Gln at position 21 in FIG. 5 and the 20th amino acid residues after said Gln (i.e., up to Asn at position 40) completely agreed with the one deduced from the cDNA sequence. Also were found the regions of the cDNA corresponding to the remaining partial amino acid sequences which had been determined above [peptide 1: positions 125 (Ala) to 154 (Arg); peptide 2: positions 162 (Ser) to 186 (Arg); peptide 3: positions 240 (Gly) to 261 (Phe); peptide 4: positions 275 (Thr) to 288 (Val); peptide 5: positions 300 (Met) to 307 (Arg); and peptide 6: positions 325 (Ala) to 336 (Asp)].

These results indicated that the cloned cDNA was the peroxidase gene. The peptide region ranging from the Met encoded by the initiator codon ATG to the 20th residue deduced from the nucleotide sequence was not found in the mature form of the peroxidase, and thus it seemingly corresponded to a signal peptide.

EXAMPLE 3

Expression of peroxidase protein in yeast

The full-length cDNA was excised from the clone C13 containing the full-length cDNA of Arthromyces peroxidase obtained in Example 2 and inserted into a yeast expression plasmid. Thus a peroxidase expressing plasmid in yeast was constructed.

Figure 1:
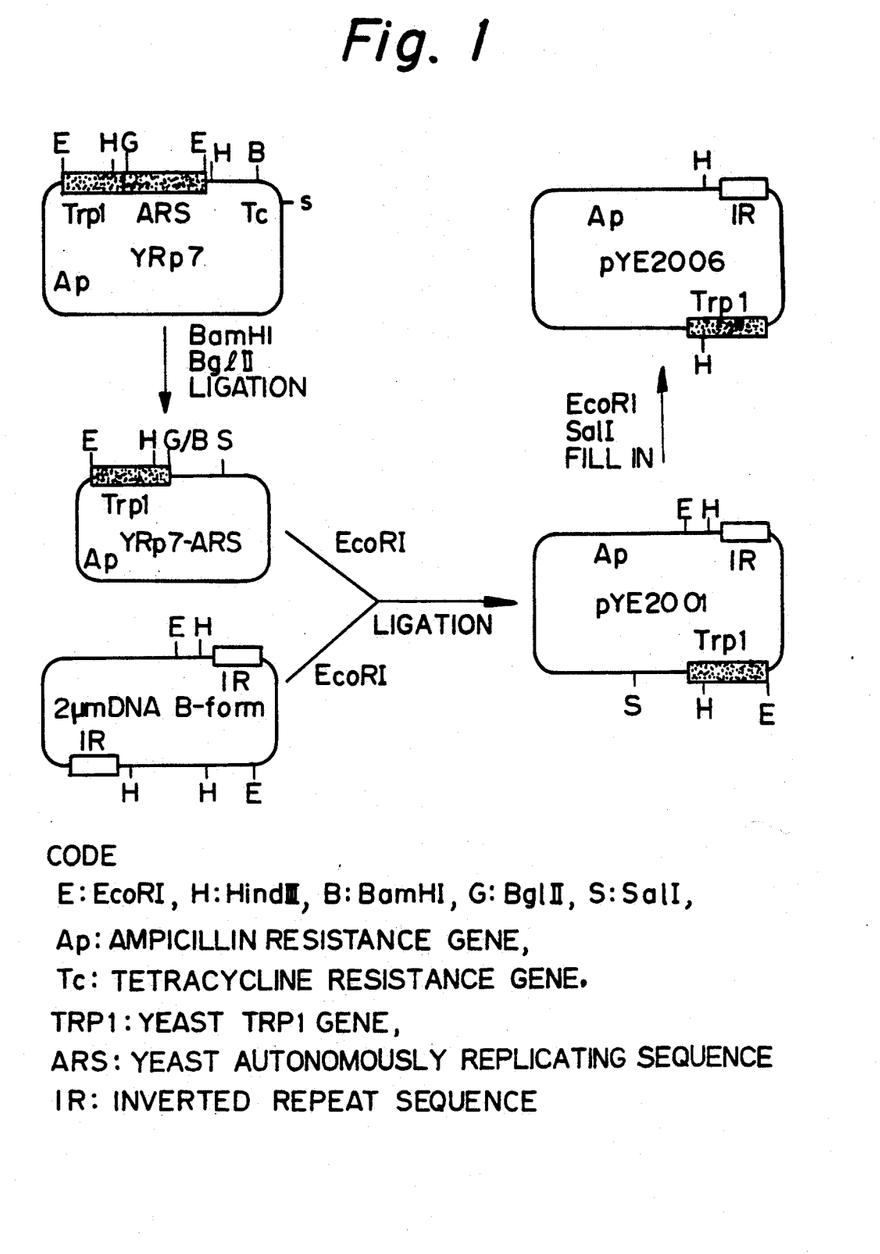
FIG. 1 illustrates the steps to the formation of an intermediate plasmid pYE2006 in the construction of plasmid pYEPOD1 which expresses the peroxidase protein in yeast.

(1) As the yeast expression plasmid, pYE22m constructed by the following method was employed. The ARS region (autonomous replication site in yeast chromosome) was removed from YRp7 [refer to Struhl, K. et al., Proc. Natl. Acad. Sci. USA, 76, 1035–1039 (1979); Stinchcomb, D. T. et al., Nature, 282, 39–43 (1979); Tschumper, G and Carbon, J., Gene, 10, 157–166 (1980) (FERM BP-3355)] with BamHI and BglII. To the EcoRI site of the resulted plasmid YRp7-ars, an EcoRI fragment containing an IR region (inverted repeat) of 2 μm DNA B-form was inserted to construct pYE2001. A plasmid which was obtained by removing the two EcoRI sites and SalI site from pYE2001 by fill-in treatments was referred to as pYE2006 (FIG. 1). To the HindIII site of this pYE2006 adjacent to the IR region, a glyceraldehyde 3-phosphate dehydrogenase gene (GAPDH) of 2.1 kb obtained from yeast chromosome [refer to Holland J. P., Holland M. J., J. Biol. Chem., 245, 9839–9845 (1979); Ashikari, T. et al., Appl. Microbiol. Biotechnol., 30, 515–520 (1989)] was inserted to form pYE2011.

Figure 2:
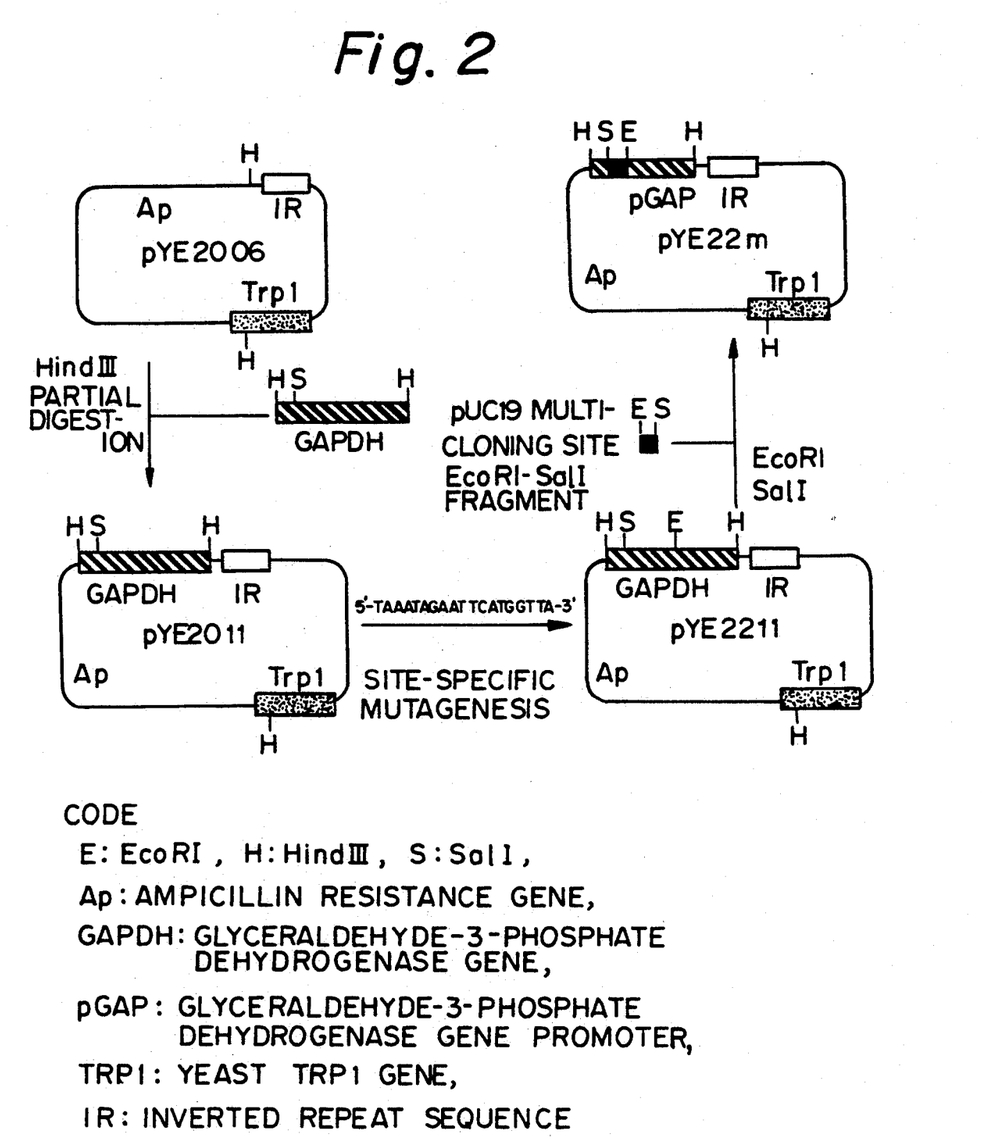
FIG. 2 illustrates the steps from pYE2006 to pYE22m.

An EcoRI site was introduced into the upstream of the GAPDH structural gene of pYE2011, adjacent to initiation codon, by the site-specific mutagenesis with a synthetic DNA 5'-TAAATAGAATTCATGGTTA-3', (see SEQ ID NO: 11) to thereby construct plasmid pYE2211 [Ashikari, T. et al., Appl. Microbiol. Biotechnol., 30, 515–520 (1989)]. The GAPDH structural gene region was deleted from pYE2211 with EcoRI and SalI and the EcoRI-SalI multi-cloning site of pUC19 was inserted in place, thus constructing a plasmid pYE22m (refer to FIG. 2).

Figure 3:
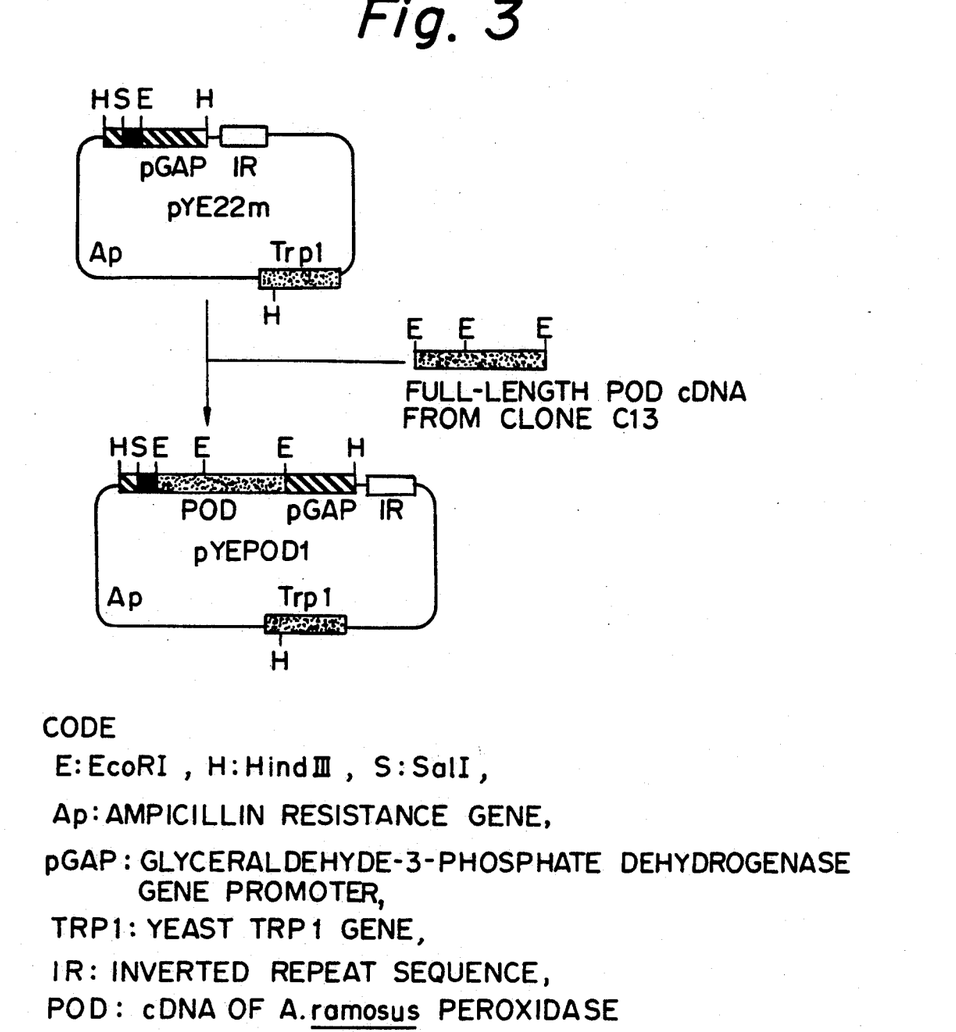
FIG. 3 illustrates the steps from pYE22m to the final pYEPOD1 plasmid.

A fragment of approximately 1.4 kbp obtained by partially digesting the C13 clone with EcoRI, which contained the full-length cDNA fragment of POD, was ligated with a fragment of approximately 8.3 kbp obtained by digesting pYE22m with EcoRI. The plasmid thus obtained was referred to as pYEPOD1 (FIG. 3). POD should be expressed in this plasmid under the control of glycelaldehyde 3-phosphate dehydrogenase promoter. A yeast strain S. cerevisiae G-1315 (Mat α, trip1) [H. Yoshizumi et al., J. Jpn. Soc. Starch Sci., 34, 148 (1987)] was transformed with this plasmid. Other strains may be used as a host, so long as they are tryptophan-requiring ones (trp1). The transformation was performed in accordance with the method reported by Ito et al. [J. Bacteriol., 153, 163 (1983)]. Thus a transformant which restored the ability to synthesize tryptophan was obtained. This transformant was referred to as G-1315 (pYEPOD1).

The transformant G-1315 (pYEPOD1) was incubated in 5 ml of Burkholder's medium [P. R. Burkholder, Am. J. Bot., 30, 206 (1943)] containing 1% casamino acids under shaking at 30° C. for 48 hours. 1 ml of the culture broth was collected and the supernatant was concentrated approximately 50-fold by Ultra-Free C3GC (Milipore Co.). The yeast cells were treated by the method of Yaffe et al. [Proc. Natl. Acad. Sci. USA, 81, 4819 (1984)] to obtain proteins.

Figure 4:
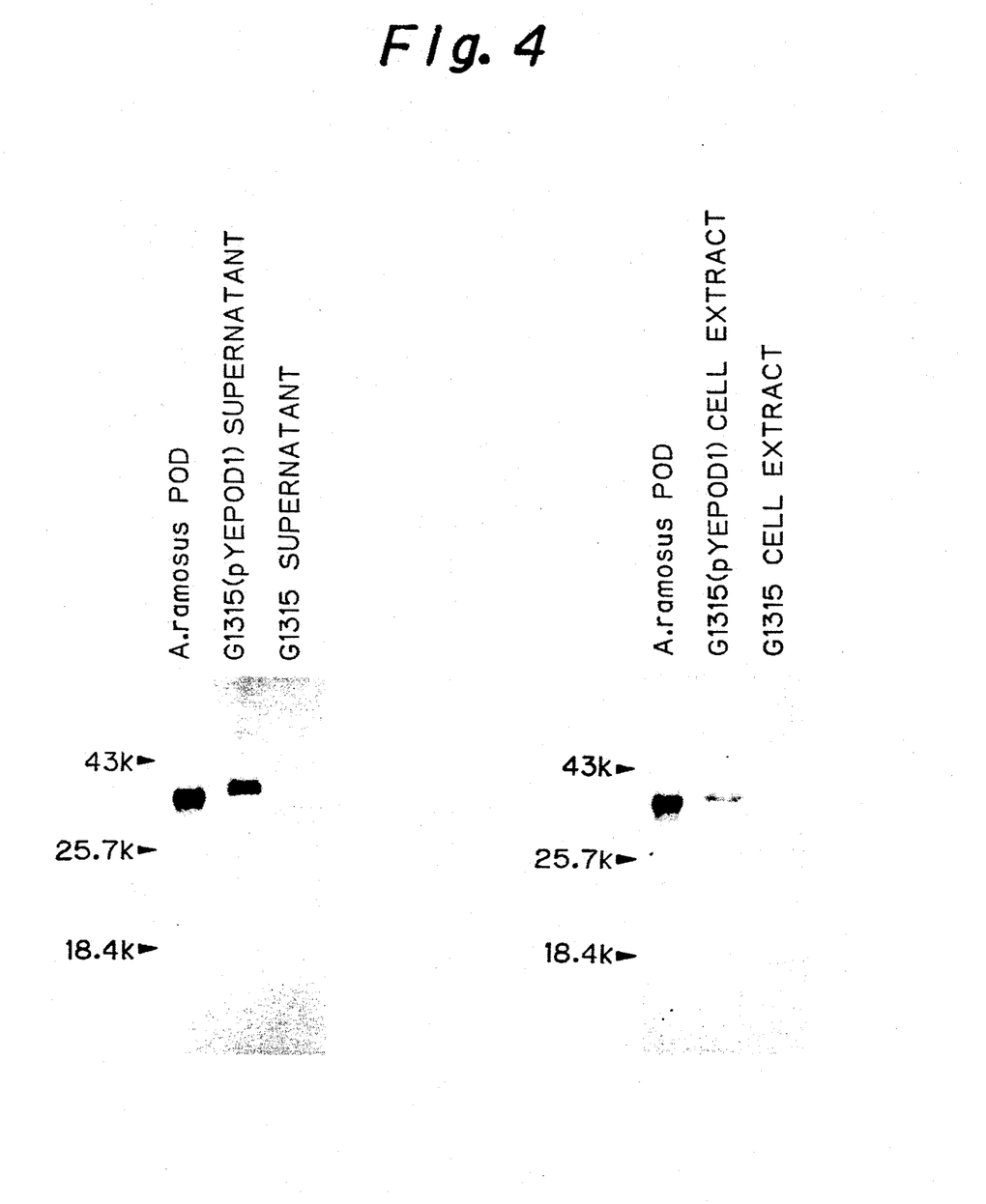
FIG. 4 illustrates electrophoretic patterns showing that the yeast transformed with pYEPOD1 produced the peroxidase protein.

These proteins were separated by SDS polyacrylamide electrophoresis and then subjected to Western blotting on a nylon membrane to detect those which reacted with anti-Arthromyces peroxidase antibody in the enzyme-labelled antibody method [refer to, for example, Imabori et al., Zoku Seikagaku Jikken Kosa: Tanpakushitsu no Kagaku, Tokyo Kagaku Dojin (1987)]. As a result, a single band was observed at almost the same position as that of the Arthromyces peroxidase protein in both of the extracellular and intracellular fractions. Since a plasmid-free host GH1315 did not exhibit such a band, it was confirmed that the Arthromyces peroxidase protein was produced by the recombinant yeast (FIG. 4).

(3) Next, the peroxidase activities in the supernatant and the cells were determined (using the rest of the culture (4 ml). The cells and the supernatant were separated. The enzyme activity in the supernatant was measured as such. The cells were suspended in 1 ml of a 10 mM potassium phosphate buffer solution and disrupted by ultrasonication. After centrifuging, the supernatant was used as a crude enzyme solution.

The enzyme activity was determined by the following method. To 1 ml of a 0.1M potassium phosphate buffer solution (pH 7.0), 1.3 ml of a 11.5 mM phenol solution, 0.25 ml of a 10 mM 4-aminoantipyrine solution and 0.2 ml of a 6 mM hydrogen peroxide solution were added. After pre-heating the mixture at 37° C., 0.25 ml of the sample was added and the mixture was reacted for 5 minutes. After the completion of the reaction, 0.2 ml of a 20% sodium azide solution was added and the absorbance at 500 nm was measured. The obtained value was referred to as a reaction value. Separately, a control value was determined by adding 0.2 ml of a 20% sodium azide solution before adding the sample and then the reaction was performed. The absorbance measured in the same manner was referred to as the control value. The titer of the peroxidase was expressed in Unit (U), namely, the amount of the enzyme capable of consuming 1 mol of hydrogen peroxide within 1 minute was referred to as 1 U. The titer (U/ml) of the sample peroxidase was calculated in accordance with the following equation.

Titer (U/ml)=$0.396 \times \Delta A_{500} \times$ (dilution ratio of sample);

wherein $\Delta A_{500}$ represents the difference between a reaction value and a control value.

As a result of the measurement, it was found that the extracellular supernatant showed an activity 15.6 mu/ml whereas the crude cell extract showed no activity. The protein concentration in the extracellular supernatant was 0.53 mg/ml and the specific activity of POD was 290 u/ml. Based on these data, it was estimated that approximately 0.01% of the extracellular proteins represented the active POD protein.

EXAMPLE 4

Expression of peroxidase protein in E. coli

Expression of the peroxidase in E. coli was studied. As the expression plasmid, pKK223-3 (purchased from Pharmacia) was employed. The EcoRI fragment of the clone C13, prepared by the same method as the one described above, was ligated with a fragment of approximately 4.6 kbp obtained by digesting pkk223-3 with EcoRI. The plasmid thus obtained was referred to as pKPOD1. It is believed that POD would be expressed by a tac promotor in this plasmid. An E. coli strain WA802 (ATCC 33526) (F− metB1 lacY1 galK2 galT22 λ− supE44 hsdR2) (a gift from Dr. B. Bachmann of Eschelichia coli Genetic Stock Center) was transformed with this plasmid and thus an ampicillin-resistant transformant was obtained. This transformant was referred to as WA802 (pKPOD1).

The transformant WA802 (pKPOD1) was incubated in 2 ml of LB medium (AP 50 μg/ml, IPTG 1 mM) under shaking at 37° C. for 15 hours. Cells were harvested from 1 ml of the culture and a cellular protein fraction was prepared by the method of Yaffe et al. Proteins, reacting with anti-Arthromyces peroxidase antibody were then detected by the aforesaid enzyme-labelled antibody method. As a result, a single band was observed at the same position as that of the Arthromyces peroxidase protein. Since plasmid-free host WA802 did not exhibit such a band, it was considered that the Arthromyces peroxidase protein was produced in the recombinant E. coli.

Similar to the case of the yeast, cells were harvested from the residual culture (1 ml) and a crude cell extract was prepared. Although the peroxidase activity was examined, it showed no peroxidase activity.

According to the present invention, the cDNA of a peroxidase gene of microbial origin has been provided and the nucleotide and amino acid sequences thereof have been clarified. A yeast and E. coli transformed with a plasmid containing the aforesaid cDNA produce the protein identical with the Arthromyces peroxidase. In fact, the enzyme activity was detected in the case of the yeast. Thus the present invention has enabled the production of the peroxidase of Arthromyces origin on a large scale by use of genetic engineering techniques and further to modify the peroxidase molecule through protein engineering techniques.

---

What is claimed is:

1. A process for producing a peroxidase which comprises culturing yeast host cells transformed with a recombinant vector having a peroxidase gene encoding the amino acid sequence of the following formula

MKLSLFSTFA AVIIGALALP

QGPGGGGGSV TCPGGQSTSN SQCCVWFDVL

DDLQTNFYQG SKCESPVRKI

LRIVFHDAIG FSPALTAAGQ FGGGGADGSI

IAHSNIELAF PANGGLTDTI

EALRAVGINH GVSFGDLIQF ATAVGMSNCP

GSPRLEFLTG RSNSSQPSPP

SLIPGPGNTV TAILDRMGDA GFSPDEVVDL

LAAHSLASQE GLNSAIFRSP

LDSTPQVFDT QFYIETLLKG TTQPGPSLGF

AEELSPFPGE FRMRSDALLA

RDSRTACRWQ SMTSSNEVMG QRYRAAMAKM

SVLGFDRNAL TDCSDVIPSA

VSNNAAPVIP GGLTVDDIEV SCPSEPFPEI

ATASGPLPSL APAP (see SEQ ID: NO 12 and 13).

and recovering and purifying a peroxidase-active substance from the culture broth, whereby enzymatically active peroxidase is obtained without incubation of the peroxidase with heme 2. A process according to claim 1, wherein the enzymatically active peroxidase is secreted from the yeast host cells into the culture broth and the secreted peroxidase is recovered and purified from the culture broth.

* * * * *